United States Patent [19]

Arnsten et al.

[11] Patent Number: 4,847,300

[45] Date of Patent: Jul. 11, 1989

[54] USE OF ALPHA-2I SELECTIVE ADRENERGIC RECEPTOR AGONISTS IN MEMORY ENHANCEMENT

[75] Inventors: Amy F. T. Arnsten, Bethany; Patricia S. Goldman-Rakic, Hamden, both of Conn.

[73] Assignee: Yale University, New Haven, Conn.

[21] Appl. No.: 928,442

[22] Filed: Nov. 7, 1986

[51] Int. Cl.$^4$ .......................................... A61K 31/165
[52] U.S. Cl. ................................................... 514/617
[58] Field of Search ........................................ 514/617

[56] References Cited

PUBLICATIONS

Thomas J. Brozoski, Roger M. Brown, H. E. Rosvold and Patricia S. Goldman, "Cognitive Deficit Caused by Regional Depletion of Dopamine in Prefrontal Cortex of Rhesus Monkey", *Science*, vol. 205, 929–932, Aug. 31, 1979.

Patricia S. Goldman-Rakic and R. M. Brown, "Regional Changes of Monoamines in Cerebral Cortex and Subcortical Structures of Aging Rhesus Monkeys", *Neuroscience*, vol. 6, 177–187, 1981.

Amy F. T. Arnsten and Patricia S. Goldman-Rakic, "$\alpha_2$-Adrenergic Mechanisms in Prefrontal Cortex Associated with Cognition Decline in Aged Nonhuman Primates", *Science*, vol. 230, 1273–1276, Dec. 13, 1985.

Robert G. Mair and William J. McEntee, "Cognitive Enhancement in Korsakoff's Psychosis by Clonidine: A Comparison with L-Dopa and Ephedrine", *Psychopharmacology*, 88, 374–380, (1986).

William J. McEntee and Robert G. Mair, "Memory Enhancement in Korsakoff's Psychosis by Clonidine: Further Evidence for a Noradrenergic Deficit", *Annals of Neurology*, 7, 466–470, (1980).

Raymond T. Bartus, Denise Fleming and H. R. Johnson, "Aging in the Rhesus Monkey: Debilitating Effects on Short-Term Memory[1]", *Journal of Gerontology*, 33, 858–871, (1978).

Eugene M. Sorkin and Rennie C. Heel, "Guanfacine A Review of Its Pharmacodynamic and Pharmacokinetic Properties, and Therapeutic Efficacy in the Treatment of Hypertension", *Drugs*, 31, 301–336, (1986).

C. D. Frith, J. Dowdy, I. N. Ferrier and T. J. Crow, *Psychopharmacology*, 87, 490–493, (1985).

C. L. Boyajian, S. E. Loughlin and F. M. Leslie, *Neurosci Abstracts*.

Chem. Abst. 93-125813u (1980).

*Primary Examiner*—Stanley J. Friedman
*Attorney, Agent, or Firm*—Sprung, Horn, Kramer & Woods

[57] ABSTRACT

Disclosed is a method of treating memory disorders and cognitive decline, e.g., age-related cognitive decline, in a primate by administering thereto a therapeutically effective amount of an alpha-2 agonist having a high affinity for the alpha-2I subtype, e.g., guanfacine and guanabenz or a nontoxic, pharmaceutically acceptable salt thereof. Particularly preferred is the use of alpha-2I selective agonists such as guanfacine.

17 Claims, 3 Drawing Sheets

USE OF ALPHA-2I SELECTIVE ADRENERGIC RECEPTOR AGONISTS IN MEMORY ENHANCEMENT

GOVERNMENT RIGHTS

This invention was made with United States government support under contracts RO1 MH 38546 and KO5MH00298 from the National Institute of Mental Health and Contract RO1 AG06036-01 from the National Institute of Aging.

BACKGROUND OF THE INVENTION

1. Field of the Invention

The present invention concerns improvement of memory in primates, particularly in normal aged primates. The present invention particularly relates to improvement of short term memory in aged primates using alpha-2 adrenergic receptor agonists that have a high affinity for the alpha-2I subtype, e.g., guanfacine and guanabenz.

2. Background Information

Recently, there has been increased awareness for memory loss problems in individuals. Particular attention has been directed to Alzheimer's Disease which generally inflicts only the middle aged to elderly. Alzheimer's Disease is thought to afflict 5% of those over 65 years and 15% of those over 80. At the present time, there is no effective treatment for this disease, nor is there any agent that can reliably improve memory in normal aged humans. Other memory disorders include Korsakoff's Amnesia and "benign senescence" in normal aged individuals.

As reported by Thomas J. Brozoski, Roger M. Brown, H. E. Rosvold and Patricia S. Goldman, "Cognitive Deficit Caused by Regional Depletion of Dopamine in Prefrontal Cortex of Rhesus Monkey", Science, Vol. 205, 929-932, Aug. 31, 1979, depletion of the catecholomines, norepinephrine and dopamine, in a circumscribed are of association cortex in rhesus monkeys produced an impairment in the performance of a working memory task, spatial delayed alternation. This behavioral deficit was found to be pharmacologically reversed with catecholomine agonists such as L-dopa, apomorphine and clonidine.

Patricia S. Goldman-Rakic and R. M. Brown, "Regional Changes of Monoamines in Cerebral Cortex and Subcortical Structures of Aging Rhesus Monkeys", Neuroscience, Vol. 6, 177-187, 1981, noted that deterioration in sensory, motor and cognitive functions is a frequent accompaniment of old age. The article further reported that since these functions depend heavily on the integrity of neocortical mechanisms, their loss with age may be due to structural and/or functional alterations which are reflected in the neurochemistry of the aging cortex. Still further, the article indicated that studies of the elderly human brain have revealed decrements in catecholamines, indoleamines, acetylcholine and gamma-aminobutyric acid. Studied therein were the endogenous concentrations and biosynthetic activity of dopamine, norepinephrine and serotonin in selected cortical and subcortical regions of the brain in rhesus monkeys. The paper reported significant loss of catecholamines in the aged monkey brain, particularly in the prefrontal cortex.

Heretofore, clonidine, an alpha-2-agonist and a known antihypertensive, has been shown to improve the memory of aged monkeys (Amy F. T. Arnsten and Patricia S. Goldman-Rakic, "°2-Adrenergic Mechanisms in Prefrontal Cortex Associated with Cognition Decline in Aged Nonhuman Primates", Science, Vol. 230, 1273-1276, Dec. 13, 1985). Clonidine, however, suffers from certain disadvantages. Clonidine's memory-enhancing effects generally occur only at high doses (e.g., 0.01 to 0.09 mg/kg), which also produce profound hypotension and sedation. These side-effects have hindered clinical trials of the use of clonidine in treating memory disorders.

Receptor binding data provides evidence for two distinct alpha-2 receptor sub-types, C. L. Boyajian, S. E. Loughlin and F. M. Leslie, Neurosci. Abstracts, Department of Pharmacology, University of California, Irvine, Calif. One subtype binds with high affinity to the antagonist idazoxan, and is referred to as the "alpha-2I subtype"; the other subtype binds with high affinity to both idazoxan and to the antagonist, rauwolscine, and is referred to as the "alpha-2R subtype".

Heretofore, guanfacine, an alpha-2-adrenergic agonist, was used to decrease blood pressure.

SUMMARY OF THE INVENTION

In accordance with the present invention, it has been discovered that alpha-2I selective agonists, that have a high affinity for the alpha-2I subtype, i.e., that have a low alpha-2I/alpha-2R $K_i$ ratio, e.g., guanfacine and guanabenz and their nontoxic pharmaceutically acceptable salts are useful in treating memory disorders and cognitive decline, e.g., age-related cognitive decline, in primates, including humans and simian species, particularly in normal aged primates, without significant induction of hypotension or sedation. In one aspect, this invention provides a method of treating cognitive decline, e.g., age-related cognitive decline associated with catecholamine deficiency, and memory disorders, e.g., Alzheimer's disease, Korsakoff's amnesia and benign senescence, in primates, especially normal aged primates, by administering thereto a therapeutically effective amount of an alpha-2 agonist having a high affinity for the alpha-2I subtype, e.g., guanfacine, or a nontoxic, pharmaceutically acceptable salt thereof. In another aspect, the invention also provides a method of improving age related cognitive performance (e.g., age-related short term memory deficit and short-term memory related task performance) in a primate, especially a normal aged primate, which method comprises administering thereto a therapeutically effective amount of an alpha-2 agonist having a high affinity for the alpha-2I subtype, e.g., guanfacine or a nontoxic pharmaceutically acceptable salt thereof.

Dosages of from at least about 0.0000001 mg/kg, up to at least about 0.01 mg/kg are effective, preferably by injection or orally. Guanfacine is often effective in the nanogram/kg range (although both higher and lower doses can be effective in individual animals), while guanabenz shows more consistent improvement without side effects in the picogram/kg range. Dosages within these ranges can be administered at intervals sufficient to maintain a therapeutic effect, from multiple daily doses to single doses on non-sequential days.

DETAILED DESCRIPTION OF THE INVENTION

The present invention is based on the observation that the administration of an alpha-2 agonist that has a high affinity for the alpha-2I subtype, e.g., guanfacine or guanabenz or a nontoxic, pharmaceutically acceptable salt thereof, or more particularly an alpha-2 agonist which like guanfacine is selective for the alpha-2I receptor subtype, have been effective in treating age-related cognitive decline and improving cognitive performance in normal aged primates, with concomitant minimal hypotensive or sedative side-effects. This has been particularly noted in improvements relating to short term memory, in treating short term memory deficits and in improving short term memory in aged subjects.

The active compound of the present invention, namely, an alpha-2 agonist that has a high affinity for the alpha-2I subtype can be administered as a medicament, i.e., a pharmaceutical composition.

The pharmaceutical compositions used in the methods of this invention for administration to animals and humans are comprised of, as active ingredients, at least one alpha-2 agonist having a high affinity for the alpha-2I subtype, in association with a pharmaceutical carrier or excipient.

The medicament can be in the form of tablets (including lozenges and granules), dragees, capsules, pills, ampoules or suppositories comprising the compound of the invention.

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of the active compound of the invention in association with a carrier and/or enclosed within an envelope. Whether the medicament contains a daily dose, or for example, a half, a third or a quarter of a daily dose will depend on whether the medicament is to be administered once or, for example, twice, three times or four times a day, respectively.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, will of course be determined according to standard medical principles under the direction of a physician or veterinarian.

The active compound can also be administered as suspensions, solutions and emulsions of the active compound in aqueous or non-aqueous diluents, syrups, granulates or powders.

Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agaragar, calcium carbonate and sodium bicarbonate; (e) agents for retarding dissolution, e.g., paraffin; (f) resorption accelerators, e.g, quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethyl glycols.

The tablets, dragees, capsules and pills comprising the active compound can have the customary coatings, envelopes and protective matrices, which may contain opacifiers. They can be so constituted that they release the active ingredient only, or preferably in a particular part of the intestinal tract, possibly over a period of time. The coatings, envelopes and protective matrices may be made, for example, from polymeric substances or waxes.

The active ingredient can also be made up in microencapsulated form together, with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, [e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, solutions and emulsions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface-active agents (e.g., ethoxylated isostearyl alcohols, polyoxyethylene sorbite and sorbitane esters), microcrystalline cellulose, aluminium metahydroxide, bentonite, agar-agar and tragacanth or mixtures thereof.

The pharmaceutical compositions can also contain coloring agents and preservatives, as well as perfumes and flavoring additions (e.g., peppermint oil and eucalyptus oil) and sweetening agents (e.g., saccharin and aspartame).

The pharmaceutical compositions will generally contain from 0.5 to 90% of the active ingredient by weight of the total composition.

In addition to the active compound, the pharmaceutical compositions and medicaments can also contain other pharmaceutically active compounds.

Any diluent in the medicaments of the present invention may be any of those mentioned above in relation to the pharmaceutical compositions. Such medicaments may include solvents of molecular weight less than 200 as the sole diluent.

It is envisaged that this active compound will be administered perorally, parenterally (for example, intramuscularly, intraperitoneally, subcutaneousyy, transdermally or intravenously), rectally or locally, preferably orally parenterally, especially perlingually, or intravenously. Preferred pharmaceutical compositions and medicaments are, therefore, those adapted for administration such as oral or parenteral administration. Administration in the method of the invention is preferably oral or parenteral administration.

It may at times be necessary to deviate from the aforementioned dosage rates, and in particular to do so as a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than the above-mentioned minimum dosage rate, whilst other cases the upper limit mentioned must be exceeded to achieve the desired results. Where larger amounts are administered, it may be advisable to divide these into several individual administrations over the course of the day.

The present invention is based on the observation that guanfacine, guanabenz and similar alpha-2 agonists that have a high affinity for the alpha-2I subtype and preferably alpha-2 selective agonists, e.g., guanfacine, are useful in treating memory disorders, e.g., age-related memory disorders in which short-term memory loss is believed to be associated with catecholamine dysfunction in the brain. It has been reported that the catecholamine, norepinephrine, is markedly decreased in two diseases associated with profound memory loss, namely Alzheimer's Disease (Adolfsson et al, *Brit. J. Psychiat.,* 135, 216–223 (1979); Benton et al *Lancet,* 20, 456 (1982); Perry et al, *J. Neurol. Sci.,* 51, 279–287 (1981): Forno, *Neuropath. Exp. Neurol.,* 37, 614 (1978); Tomlinson et al, *J. Neurol. Sci.,* 49, 419–428 (1981) and Iversen et al, *Neurosci. Letters,* 39, 95–100 (1983)) and Korsakoff's Amnesia (W. J. McEntee and R. J. Meir, *Ann. Neurol.,* 7, 466, (1980)). Milder norepinephrine loss is associated with normal aging in humans, and may underlie "benign senescence".

Two reports have indicated that chronic administration of the alpha-2 agonist, clonidine, (about 0.01 to 0.02 mg/kg/day for two weeks), improved memory performance in Korsakoff patients in direct relationship to the degree of norepinephrine loss, as indicated by measures in cerebral spinal fluid (McEntee and Mair, supra; R. G. Mair and W. S. McEntee, *Psychopharm.,* 88, 274–280, (1986). Thus, alpha-2 agonists appear to be able to replace lost norepinephrine and improve cognitive performance. However, neither of these studies reported clonidine's effects on blood pressure or sedation, and it is known that lower clonidine dosages (about 0.003 mg/kg) produce a substantial lowering of blood pressure, as well as sedative side effects in normal adult volunteers (C. D. Frith, J. Dowdy, I. N. Ferrier and T. J. Crow, *Psychopharmacology,* 87, 490–493, (1985)). In a preliminary trial with Alzheimer patients, acute clonidine administration produced such severe hypotension and sedation that the study was terminated.

The alpha-2 agonist clonidine has a higher affinity for the alpha-2R, than the alpha-2I, showing a $K_i$ ratio for alpha-2R/alpha-2I of 27.7/38.1 (the smaller the Ki value, the higher the affinity). In contrast thereto, the alpha-2 agonist guanfacine exhibits an opposite profile, with high selectivity for the alpha-2I subtype (340.0/22.6). Without wishing to be bound by any particular theory of operability, it is believed that the ability of alpha-2 drugs to improve memory is due to their actions at the alpha-2I subtype, while the hypotensive, sedative and memory impairing effects of these drugs are due to actions at the alpha-2R subtype.

The above belief led to a reasonable inference that guanfacine would improve memory at very low doses, since it has high affinity for the alpha-2I As its affinity for the other subtype, alpha-2R, is very poor, it was believed that quite high doses would be needed to lower blood pressure, produce sedation and diminish memory enhancement. The opposite profile would be predicted for clonidine; low doses should impair memory, lower blood pressure, and begin to produce sedation, while memory improvement should be observed at higher doses. These contrasting dose/response profiles were indeed observed as will be described in the Examples hereinbelow.

EXAMPLES

General

The examples described herein report an evaluation of the effects of alpha-2 adrenergic agonists on memory performance, blood pressure and sedation in monkeys.

Subjects

The animals used in the following examples were 13 female rhesus monkeys ranging in age from 17 to 30 years. As actual birth dates were not available for the majority of these animals, ages were estimated on the basis of prior breeding and testing records, as well as on dental records and general appearance. Monkeys in this age range are known to have naturally occurring catecholamine loss (Goldman-Rakic and Brown, supra) and poor memory as measured on the delayed response task (T. T. Bartus, D. Fleming & H. R. Johnson, *J. Gerontol.,* 33, 858, (1978); Arnsten and Goldman-Rakic, *Science,* 230, 1273, (1985)).

The average lifespan of a rhesus monkey in the wild is 15 to 20 years.

Memory Testing

In the following examples, memory was assessed using a version of the delayed response task, variable delayed response The delayed response task is considered a sensitive measure of spatial working memory (Goldman and Rosvold, *Exp. Neurol.,* 27, 291–304, (1970)). To observe the effects of each drug on mnemonic capacity, the delays were varied between "0" seconds and the temporal interval at which each animal performed at chance. Five different delay lengths were used in the 30 trials which made up a daily test session. Animals were tested twice a week. All drug responses were compared to matched placebo control sessions The experimenter testing the animal was unaware of the drug treatment conditions.

Sedation Assessment

Sedation was rated using a 5 point scale where 0=normal level of arousal, I=quiet, II=sedated, III-=intermittent sleeping and IV=too sedated to test.

Drug Administration

All drug solutions were made up fresh each day under sterile conditions. Drugs were diluted in sterile saline and injected intramuscularly 15 minutes (all drugs) or two hours (guanfacine and guanabenz only) prior to memory testing. Generally, a single dose of the drug was administered each week; extended washout periods were necessary for guanfacine given the longer half-life of this drug.

Data Analysis

Delayed response performance on the drug was compared to matched placebo (saline) control for the same week, and the drug effect was expressed as % change from placebo control As the animals served as their own controls; statistical analyses employed repeated measures designs ($t_{dep}$, 1-ANOVA-R) Differences in sedation score data were assessed using a nonparametric, repeated measures analysis (Wilcoxon test).

Blood Pressure Study

In order to measure blood pressure in the awake, behaving monkey, three aged animals were adapted to primate chair restraint for several weeks.

Blood pressure was measured using a pediatric digital blood pressure monitor.

Each day the animals were chaired and then immediately injected with the drug or saline. Fifteen minutes later, three blood pressure measurements were taken. The animal was then tested on delayed response for approximately 30 minutes. Following memory testing, three more blood pressure measurements were taken before the monkey was returned to its home cage. The average blood pressure response before and after memory testing was calculated; drug response was compared to the previous response on saline Drug administration was initiated only after a stable blood pressure baseline was apparent.

All doses reported in the following Examples are equivalent (equimolar) clonidine doses.

EXAMPLE 1

THE EFFECT OF ADMINISTERING CLONIDINE TO AGED MONKEYS

Early experiments with the alpha-2 agonist, clonidine, demonstrated improved memory in 5/5 aged monkeys (Arnsten and Goldman-Rakic, *Science*, 230, 1273–1276, (1985)). This result was replicated in eight (8) additional aged monkeys (1-ANOVA-R, significant effect of clonidine dose $F(4,28)=17.86$, $p <0.001$).

On the average, the optimal clonidine dose for improving memory was 0.05 mg/kg (see Table 1 hereinbelow). This dose of clonidine produced a profound reduction in blood pressure (a drop of greater than 50 mm Hg systolic). Marked sedation was also observed in this dose range (average sedation score=II, $p<0.01$ compared to saline, Wilcoxon test - see Table 2 hereinbelow). When the dose of clonidine was lowered (0.0001 to 0.01 mg/kg), hypotension was less severe (approximately 10 to 30 mm Hg drop). However, these doses of clonidine often impaired memory, presumably due to their inhibitory actions at pre-synaptic receptors (see Table 2 and FIGS. 1 and 3). It is notable that low doses of clonidine (about 0.003 mg/kg) also have been reported to impair cognitive abilities, lower blood pressure (20 mm Hg drop), and induce sedation in humans (Frith, Dowdy, Ferrier and Crow, supra).

Sensitivity to the drug varied widely between animals, as is indicated by the large differences in optimal clonidine dose for each aged monkey as described in Table 1. Thus, an optimal dose for one monkey was often an inhibitory dose for another. This variability accounts for the low mean improvement shown in Table 2. However, despite quantitative variation in drug sensitivity, all animals showed the same qualitative dose/response profile with clonidine: low doses produced no effect or memory impairment, while higher doses improved memory, induced sedation, and produced marked reductions in blood pressure. Thus, the effective clonidine dose range for memory improvement is also the range where serious hypotensive and sedative side effects are observed.

EXAMPLE 2

THE EFFECTS OF ADMINISTERING GUANFACINE TO AGED MONKEYS

The applicants have discovered that the alpha-2 agonist, guanfacine, showed the opposite dose response profile from clonidine; low doses of this drug improved memory while only the high doses impaired memory, lowered blood pressure and induced sedation (see Table 2; as with clonidine, variations in drug sensitivity resulted in low mean scores; see Table 1 for individual data). Low doses of guanfacine significantly improved memory in 11/11 aged monkeys (Table 1; $p<0.001$, $t_{dep}$ on optimal dose vs. saline), without any hypotensive or sedative side effects (average change in systolic blood pressure=+6 mm Hg, sedation scores=0). These memory effects may be long lasting, typically up to four days and occasionally much longer. Guanfacine improved memory at doses significantly lower than those needed with clonidine (an average of about 0.001 mg/kg as compared to 0.05 mg/kg for clonidine, $p<0.01$, $t_{dep}$). Profound hypotension and sedation were observed only after extremely large doses of guanfacine (0.1 to 0.5 mg/kg; see FIG. 3). This 100 fold difference between the guanfacine doses capable of improving memory and those where unwanted side effects appear make guanfacine far superior to clonidine for treating memory disorders. In clinical trials, guanfacine's hypotensive effects similarly appeared only in the higher dose range; guanfacine is 1/10 as potent as clonidine in clinical blood pressure studies (E. M. Sorkin and R. C. Heel, *Drugs*, 31, 301–336, (1986)).

Figure 1:
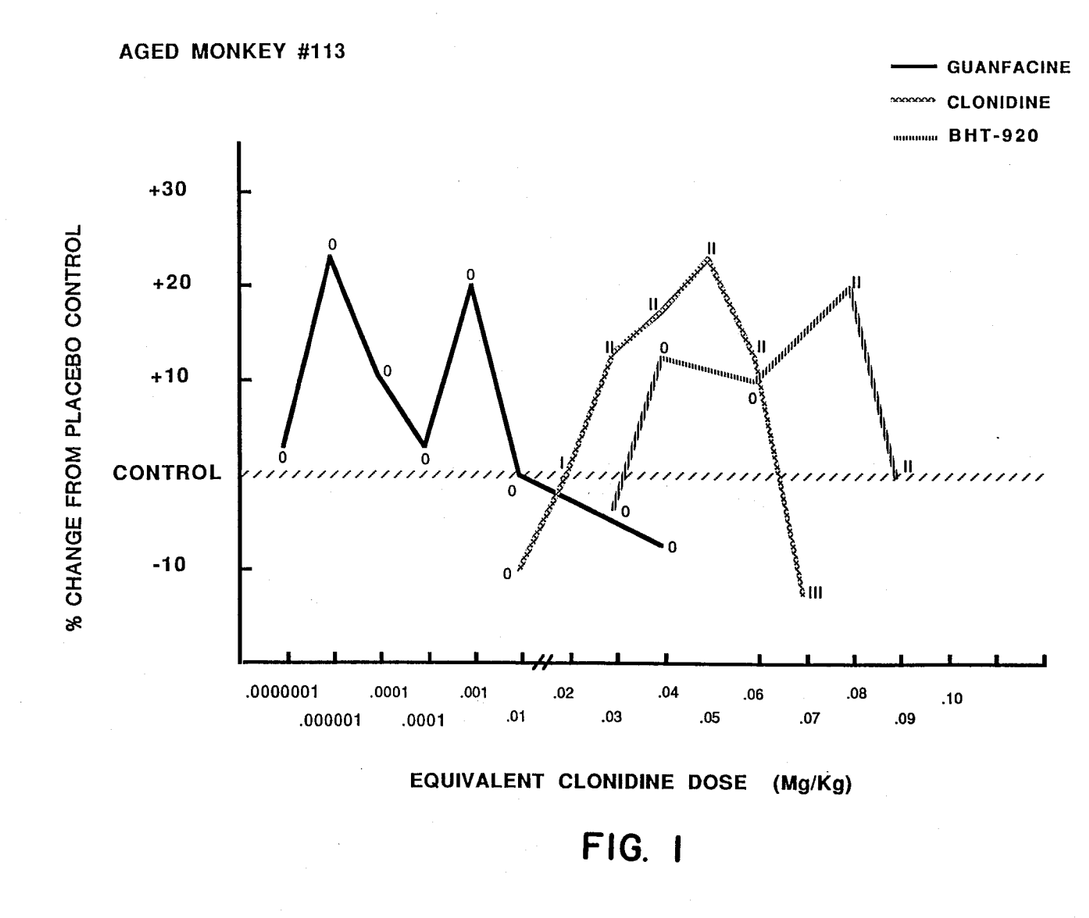
FIG. 1 is a graph of % change in memory performance from placebo control vs. equivalent (equimolar) clonidine dose for guanfacine (according to the invention), clonidine and BHT-920 for monkey No. 113.
Figure 2:
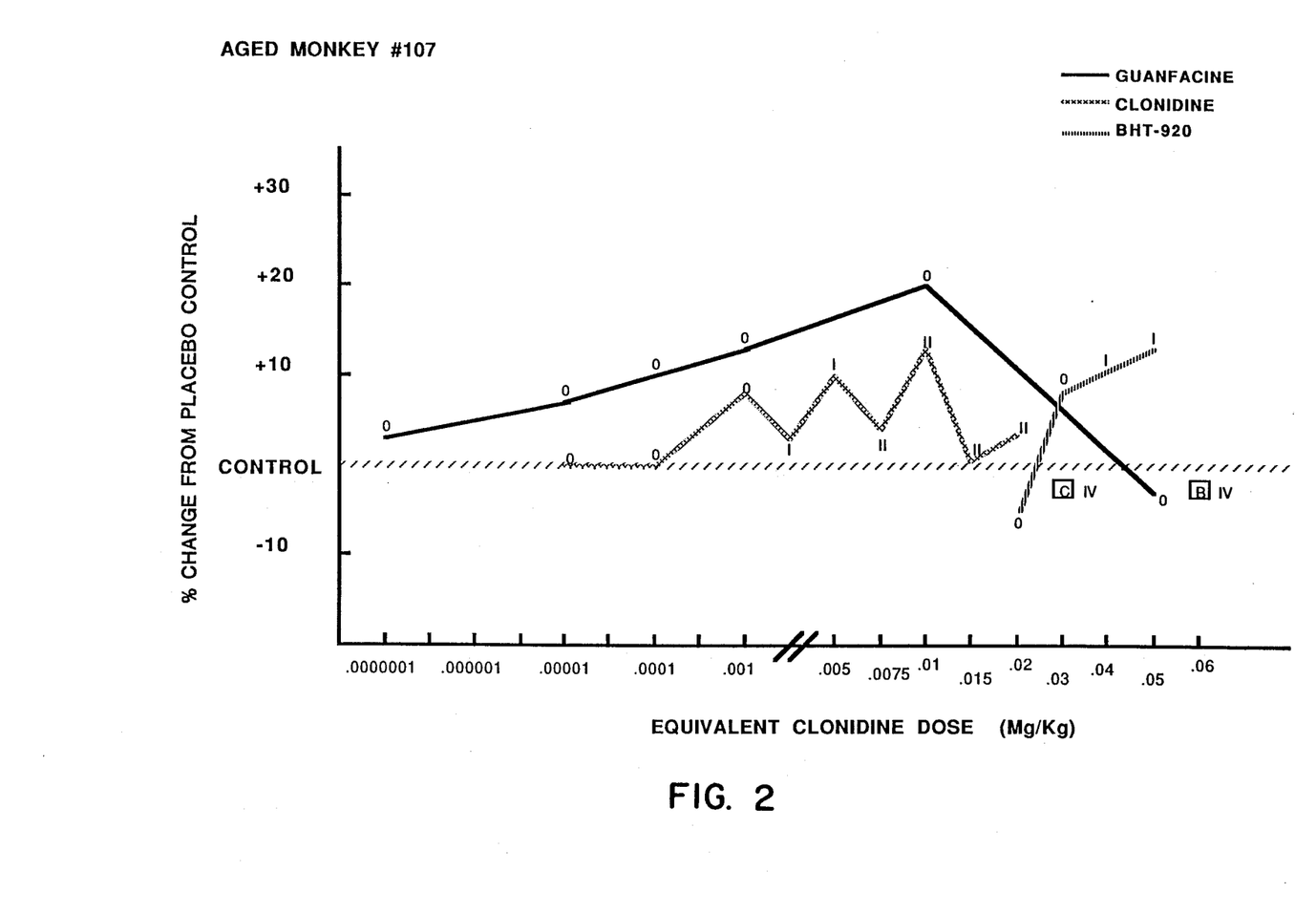
FIG. 2 is a graph of % change in memory performance from placebo control vs. equivalent (equimolar) clonidine dose for guanfacine (according to the invention), clonidine and BHT-920 for a second monkey, monkey No. 107.
Figure 3:
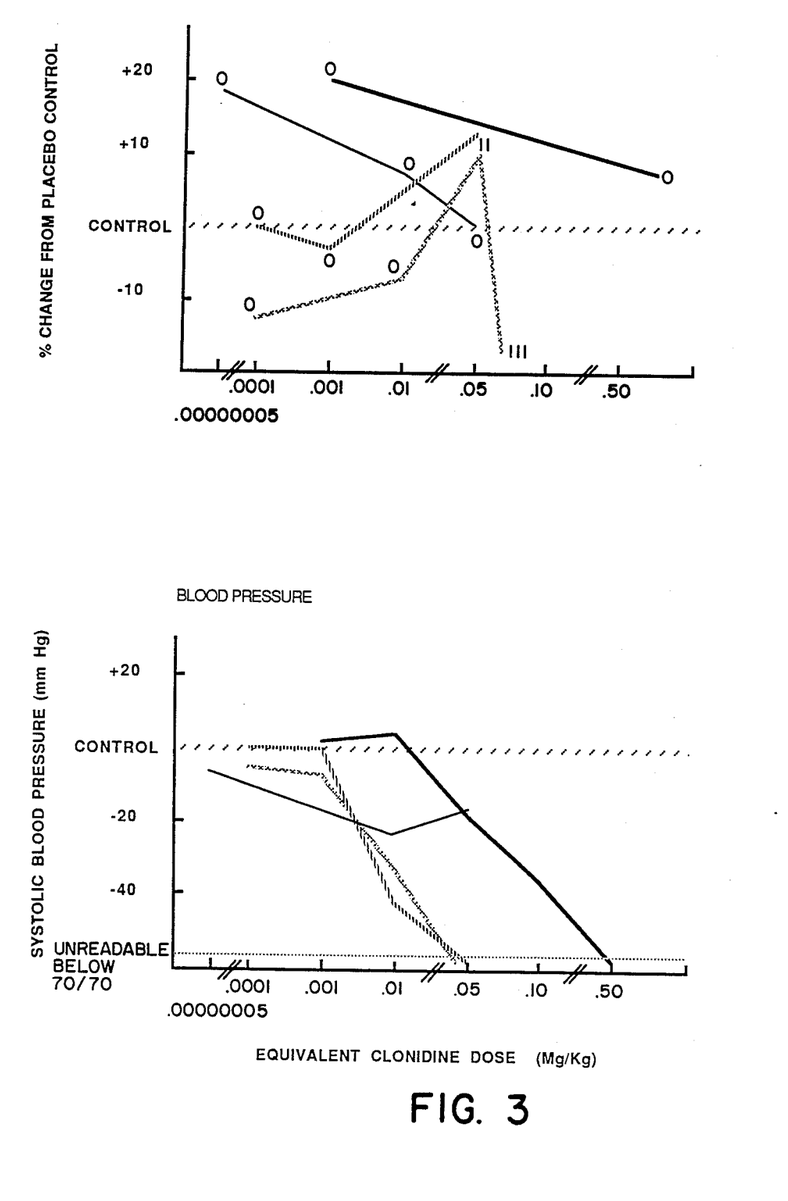
FIG. 3 is a graph of % change in memory performance (upper graph) and in systolic blood pressure (lower graph) from placebo control vs. equivalent (equimolar) clonidine dose for guanfacine (according to the invention), clonidine, BHT-920 and guanabenz (according to the invention) for a third monkey, monkey No. 445.

The differences in dose/response profiles between guanfacine and clonidine are illustrated graphically in FIGS. 1–3. These figures show the effects of clonidine (stippled line) and guanfacine (heavy solid line) on delayed response performance in three aged monkeys: #113, #107 and #445. Animal #107 was the oldest monkey in the colony (+30 years); the age of monkey #113 was estimated at about 25 years; and the age of monkey #445 was thought to be at least 17 years. Drug response was expressed as the percentage change from placebo control baseline performance for each animal; 30% is approximately perfect performance, while −20% is approximately chance performance (maximal deficit). Sedation scores were indicated for each drug dose. A sedation score of IV indicates that the animal was too sedated to test (the drug is identified by the appropriate letter inside a square). Blood pressure results for aged monkey #445 are illustrated in the lower half of FIG. 3.

It is apparent in all three figures that guanfacine improved delayed response performance at lower doses than did clonidine. Furthermore, FIG. 3 demonstrates that low doses of guanfacine improved memory without lowering blood pressure. At high doses guanfacine's beneficial effects on memory diminished (FIGS. 1-3) and hypotension was evident (FIG. 3). In contrast to guanfacine, the optimal dose of clonidine for improving memory produced severe hypotension (FIG. 3). Lower doses of clonidine produced less hypotension (FIG. 3), but often impaired memory (FIGS. 1 and 3). Thus, guanfacine improves memory at low doses and can impair or have no effect on memory at high doses, while clonidine exhibits the opposite dose/response profile. This finding is consonant with the existence of two alpha-2 receptor subtypes with opposite effects on memory.

EXAMPLE 3

THE EFFECTS OF BHT-920 AND GUANABENZ

The effects of other alpha-2 agonists were believed to behave in a similar manner on the basis of their abilities to displace idazoxan and rauwolscine from the receptor subtypes. The hypothesis predicts that those alpha-2 agonists with greater affinity for the alpha-2R than the alpha-2I will be similar to clonidine; these compounds should produce hypotension and sedation in the higher dose range where memory is improved. In contrast, those drugs that have higher affinity for the alpha-2I than the alpha-2R should be similar to guanfacine in their ability to improve memory at low doses with minimal hypotensive or sedative side effects. The greater the drug's selectivity for the alpha-2I subtype, the more specific the drug would be for memory improvement.

These predictions were realized in tests of two additional alpha-2 agonists, namely, BHT-920 (an experimental compound made by Boehringer-Ingelheim) and guanabenz. BHT-920 is two times more selective for the alpha-2R subtype (62.2/138.0) and thus it was predicted that it would be similar to clonidine. As expected, high doses of BHT-920 were needed for optimal improvement (an average of 0.07 mg/kg). These high doses produced severe hypotension (greater than 50 mm Hg drop; see FIG. 3) and sedation (average sedation score-=II) (see Table 3 hereinbelow).

FIGS. 1-3 show the effects of BHT-920 (striped line) on aged monkeys #113, #107 and #445. It is apparent that high doses of BHT-920 are needed to improve memory in these animals. FIG. 3 demonstrates that the hypotensive effects of BHT-920 are very similar to those of clonidine.

In contrast to BHT-920, guanabenz has a higher affinity for the alpha-2I than alpha-2R (36.7/5.3), however, it has a much greater affinity for alpha-2R than does guanfacine; indeed, its affinity for alpha-2R is quite similar to clonidine. It was thus believed that at very low doses guanabenz would behave similarly to guanfacine, producing a small improvement in memory without side effects. However, at slightly higher doses, interaction with the alpha-$2_R$ subtype would diminish memory improvement and begin to induce hypotension. In other words, other than at very low doses, the guanabenz response would be expected to be intermeditate between clonidine and guanfacine, in keeping with its high affinity for both receptor subtypes. This dose/response profile was observed in aged monkeys (Table 3).

The effects of guanabenz on monkey #445 are illustrated in FIG. 3 (thin solid line). Guanabenz improved memory at low doses (0.00000005–0.01 mg/kg); however, it produced more hypotensive side effects than guanfacine, but fewer side effects than clonidine. Thus, as predicted by the receptor subtype hypothesis, guanabenz had a response intermediate between guanfacine and clonidine.

SUMMARY OF THE RESULTS

The above results with the alpha-2 agonists clonidine, guanfacine, BHT-920 and guanabenz provided the first functional evidence for alpha-2 receptor subtypes, and the first evidence that memory improvement can be linked to agonist actions at one of these subtypes, the alpha-2I. These data also provide the first evidence that the hypotensive, sedating and memory impairing effects of alpha-2 agonists result from actions at the other receptor subtype, alpha-2R. Therefore, alpha-2 agonists such as guanfacine with high selectivly for the alpha-2I receptor subtype can improve memory without inducing hypotensive or sedative side effects.

TABLE 1

A COMPARISON OF THE EFFECTS OF OPTIMAL DOSES OF CLONIDINE AND GUANFACINE FOR INDIVIDUAL AGED MONKEYS

| | CLONIDINE | | | GUANFACINE | | |
|---|---|---|---|---|---|---|
| Monkey # | Dose (mg/kg) | Percent Improvement | Sedation Score | Dose (mg/kg) | Percent Improvement | Sedation Score |
| 107 | .01 | 27% | II | .01 | 20% | 0 |
| 113 | .05 | 30% | II | .000001 | 23% | 0 |
| 121 | .005 | 17% | 0 | .000001 | 10% | 0 |
| 124 | .04 | 23% | III | .0001 | 18% | 0 |
| 343 | .20 | 30% | II | .00001 | 13% | 0 |
| 444 | .03 | 25% | III | .01 | 13% | 0 |
| 445 | .04 | 18% | I | .001 | 20% | 0 |
| 446 | .08 | 17% | III | .01 | 10% | 0 |
| 447 | .06 | 23% | III | .001 | 20% | 0 |
| 448 | .07 | 30% | II | .00001 | 23% | 0 |
| 449 | .001 | 23% | 0 | .001 | 20% | 0 |

TABLE 2

THE EFFECTS OF CLONIDINE AND GUANFACINE ON MEMORY, SEDATION, AND BLOOD PRESSURE COMPARED TO MATCHED PLACEBO CONTROL

| Drug Dose (mg/kg) | Delayed Response Performance (% change from placebo control) | Sedation Score (0-IV) | Systolic Blood Pressure (mm Hg) |
|---|---|---|---|
| Clonidine | | | |
| .0001 | −6% ±2% (10)* | 0 ±0 (10) | −23 (1) |
| .001 | +3% ±4% (6) | 0 ±0 (6) | −8 ±3 (3) |
| .01 | +6% ±3% (12) | I ±I (12) | −32 ±9 (3) |
| .05 | +12% ±3% (10) | III ±I (10) | > −50 (2) |
| Guanfacine | | | |
| .0001 | +9% ±3% (6) | 0 ±0 (6) | +3 (1) |
| .001 | +10% ±5% (7) | 0 ±0 (7) | +6 ±2 (3) |
| .01 | +10% ±3% (9) | 0 ±0 (9) | −11 ±5 (3) |
| .05 | −6% ±2% (5) | 0 ±0 (5) | −21 ±3 (2) |

*Mean ± S.E.M. (n)

TABLE 3

THE EFFECTS OF BHT-920 AND GUANABENZ ON MEMORY, SEDATION AND BLOOD PRESSURE COMPARED TO MATCHED PLACEBO CONTROL

| Drug Dose (mg/kg) | Delayed Response Performance (% change from placebo control) | Sedation Score (0-IV) | Systolic Blood Pressure (mm Hg) |
|---|---|---|---|
| BHT-920 | | | |
| .0001 | 0% ±0% (2)* | 0 ±0 (2) | −9 ±9 (2) |
| .001 | −3% ±0% (2) | 0 ±0 (2) | −8 ±4 (2) |
| .01 | +9% ±1% (2) | 0 ±0 (2) | −37 ±9 (2) |
| .05 | +8% ±5% (2) | I ±0 (2) | > −50 (2) |
| .08 | +15% ±6% (3) | II ±0 (3) | |
| Guanabenz | | | |
| .00000005 | +8% ±6% (3) | 0 ±0 (3) | −7 (1) |
| .00001 | −1% ±2% (4) | 0 ±0 (4) | −20 (1) |
| .0001 | +1% ±1% (4) | 0 ±0 (4) | |
| .001 | −2% ±1% (3) | 0 ±0 (3) | −1 (1) |
| .01 | +7% ±2% (5) | 0 ±0 (5) | −11 ±2 (2) |
| .05 | +7% ±7% (2) | I ±I (2) | −16 ±4 (2) |

*Mean ± S.E.M. (n)

It will be appreciated that the instant specification and claims are set forth by way of illustration and not limitation, and that various modifications and changes may be made without departing from the spirit and scope of the present invention.

We claim:

1. A method of treating memory disorders and cognitive decline in a primate, which method comprises administering thereto a therapeutically effective amount of an alpha-2 adrenergic agonist having a high affinity or selectivity for the alpha-2I subtype or a nontoxic pharmaceutically acceptable salt thereof, said agonist having a low alpha-2I/alpha-2R Ki ratio, wherein the alpha-2 agonist is administered in an amount from 0.0000001 mg/kg to an amount that will result in concomitant no or minimal hypotensive or sedative side effects.

2. A method according to claim 1, wherein the alpha-2 agonist is selected from the group consisting of guanfacine and guanabenz.

3. A method according to claim 2, wherein the agonist is guanfacine.

4. A method according to claim 1, wherein the cognitive decline is age-related cognitive decline.

5. A method according to claim 4, wherein the age-related cognitive decline is age-related short term memory deficit.

6. A method according to claim 1, wherein the memory disorder is Alzheimer's disease.

7. A method according to claim 1, wherein the memory disorder is Korsakoff's amnesia.

8. A method according to claim 1, wherein the memory disorder is benign senescence.

9. A method according to claim 1, wherein the primate is a normal aged primate.

10. A method according to claim 9, wherein the amount is from about 0.0000001 mg/kg to 0.01 mg/kg.

11. A method of improving cognitive performance in a primate which method comprises administering thereto a therapeutically effective amount of an adrenergic alpha-2 agonist having a high affinity or selectively for the alpha-2I subtype or a nontoxic pharmaceutically acceptable salt thereof, said agonist having a low alpha-2I/alpha-2R Ki ratio, wherein the alpha-2 agonist is administered in an amount from 0.0000001 mg/kg to an amount that will result in concomitant no or minimal hypotensive or sedative side effects.

12. A method according to claim 11, wherein the primate is a normal aged primate.

13. A method according to claim 11, wherein the alpha-2 agonist is selected from the group consisting of guanfacine and guanabenz.

14. A method according to claim 13, wherein the agonist is guanfacine.

15. A method according to claim 13, wherein short-term memory is improved.

16. A method of claim 11, wherein short-term memory-related task performance is improved.

17. A method according to claim 11, wherein the amount is from about 0.0000001 mg/kg to 0.01 mg/kg.

* * * * *

UNITED STATES PATENT AND TRADEMARK OFFICE
CERTIFICATE OF CORRECTION

PATENT NO. : 4,847,300
DATED : Jul. 11, 1989
INVENTOR(S) : Arnsten et al.

It is certified that error appears in the above-identified patent and that said Letters Patent is hereby corrected as shown below:

| | |
|---|---|
| Figure 3, before 1st graph, top left side | Insert --Aged Monkey #445 Delayed Response-- |
| Figure 3, before 1st graph, top right side | Insert --____Guanfacine ____Guanabenz ........BHT-920 ~~~~Clonidine-- |
| Col. 6, line 22 | Insert --.-- after "2I" |
| Col. 6, line 60 | Insert --.-- after "response" in first instance |
| Col. 7, line 1 | Insert --.-- after "sessions" |
| Col. 7, line 26 | Insert --.-- after "control" |
| Col. 7, line 26 | Insert --.-- before "Differences" |
| Col. 7, line 44 | Insert --.-- after "saline" |
| Col. 8, line 68 | Insert --+-- before "30%" |

Signed and Sealed this

Eighteenth Day of December, 1990

Attest:

HARRY F. MANBECK, JR.

Attesting Officer

Commissioner of Patents and Trademarks